United States Patent
Keitel

(10) Patent No.: US 10,639,426 B2
(45) Date of Patent: May 5, 2020

(54) INJECTION DEVICE

(71) Applicant: Haselmeier AG, St. Gallen (CH)

(72) Inventor: Joachim Keitel, Esslingen (DE)

(73) Assignee: Haselmeier AG, St. Gallen (CH)

( * ) Notice: Subject to any disclaimer, the term of this patent is extended or adjusted under 35 U.S.C. 154(b) by 168 days.

(21) Appl. No.: 15/942,095

(22) Filed: Mar. 30, 2018

(65) Prior Publication Data
US 2018/0228973 A1 Aug. 16, 2018

Related U.S. Application Data

(63) Continuation of application No. PCT/EP2016/001598, filed on Sep. 26, 2016.

(30) Foreign Application Priority Data

Sep. 30, 2015 (DE) .................... 20 2015 006 842 U

(51) Int. Cl.
*A61M 5/20* (2006.01)
*A61M 5/315* (2006.01)
(Continued)

(52) U.S. Cl.
CPC ............ *A61M 5/2033* (2013.01); *A61M 5/20* (2013.01); *A61M 5/31553* (2013.01);
(Continued)

(58) Field of Classification Search
CPC ...... A61M 5/2033; A61M 5/20; A61M 5/482; A61M 5/31583; A61M 5/31563;
(Continued)

(56) References Cited

U.S. PATENT DOCUMENTS

| 5,114,406 A | 5/1992 | Gabriel et al. |
| 5,480,387 A | 1/1996 | Gabriel et al. |

(Continued)

FOREIGN PATENT DOCUMENTS

| DE | 102007013836 A1 | 9/2008 |
| DE | 202012001411 U1 | 5/2013 |

(Continued)

OTHER PUBLICATIONS

International search report dated Jan. 17, 2017 for corresponding international application PCT/EP2016/001600.

(Continued)

*Primary Examiner* — Bhisma Mehta
*Assistant Examiner* — Rachel T. Smith
(74) *Attorney, Agent, or Firm* — Walter Ottesen, P.A.

(57) ABSTRACT

An injection device for automatically squeezing out a dosage of injection liquid from a container. The injection device including a housing defining a longitudinal central axis; a first component; a second component; wherein the first and second component move relative to one another when the liquid is squeezed out; a spring configured to at least partially release stored energy to squeeze out the dosage; a setting device to set a rate at which the liquid is squeezed out; the setting device influencing the energy required for moving the second component relative to the first; the first component, when squeezing out liquid, is guided in the housing so as to be movable in the direction of the axis and to be rotationally fixed; and, the second component, when squeezing out liquid, is mounted relative to the housing so as to be rotatable and rotationally fixed in the direction of the axis.

13 Claims, 7 Drawing Sheets

(51) Int. Cl.
*A61M 5/48* (2006.01)
*A61M 5/31* (2006.01)

(52) U.S. Cl.
CPC .... *A61M 5/31563* (2013.01); *A61M 5/31583* (2013.01); *A61M 5/482* (2013.01); *A61M 5/3157* (2013.01); *A61M 5/31535* (2013.01); *A61M 2005/3126* (2013.01); *A61M 2205/581* (2013.01); *A61M 2205/582* (2013.01); *A61M 2205/583* (2013.01); *A61M 2205/586* (2013.01)

(58) Field of Classification Search
CPC .......... A61M 5/31553; A61M 5/31535; A61M 5/3157; A61M 2205/581; A61M 2205/582; A61M 2205/586; A61M 2205/583; A61M 2005/3126
See application file for complete search history.

(56) References Cited

U.S. PATENT DOCUMENTS

| | | | |
|---|---|---|---|
| 6,221,053 | B1 | 4/2001 | Walters et al. |
| 9,694,136 | B2 | 7/2017 | Keitel et al. |
| 2009/0048561 | A1 | 2/2009 | Burren et al. |
| 2013/0218128 | A1 | 8/2013 | Cowe |
| 2016/0317749 | A1 | 11/2016 | Jugl et al. |
| 2016/0339181 | A1 | 11/2016 | Keitel |
| 2016/0346479 | A1 | 12/2016 | Keitel |
| 2016/0361499 | A1 | 12/2016 | Keitel |
| 2018/0001031 | A1 | 1/2018 | Keitel |
| 2018/0050160 | A1 | 2/2018 | Bilton et al. |
| 2018/0221586 | A1 | 8/2018 | Keitel |
| 2018/0221587 | A1 | 8/2018 | Keitel |
| 2018/0221588 | A1 | 8/2018 | Keitel |

FOREIGN PATENT DOCUMENTS

| | | | | |
|---|---|---|---|---|
| WO | 8907463 | A1 | 8/1989 | |
| WO | 2004078241 | A1 | 9/2004 | |
| WO | 2010000085 | A1 | 1/2010 | |
| WO | 2013117332 | A1 | 8/2013 | |
| WO | 2014166891 | A1 | 10/2014 | |
| WO | 2014166900 | A1 | 10/2014 | |
| WO | 2014166918 | A1 | 10/2014 | |
| WO | WO-2014166918 | A1 * | 10/2014 | ........ A61M 5/31583 |
| WO | 2015091766 | A1 | 6/2016 | |

OTHER PUBLICATIONS

International search report dated Jan. 11, 2017 for corresponding international application PCT/EP2016/001599.
International search report dated Feb. 7, 2017 for corresponding international application PCT/EP2016/001597.
International search report dated Dec. 16, 2016 for international application PCT/EP2016/001598 on which this application is based.

* cited by examiner

Fig. 1
Fig. 2
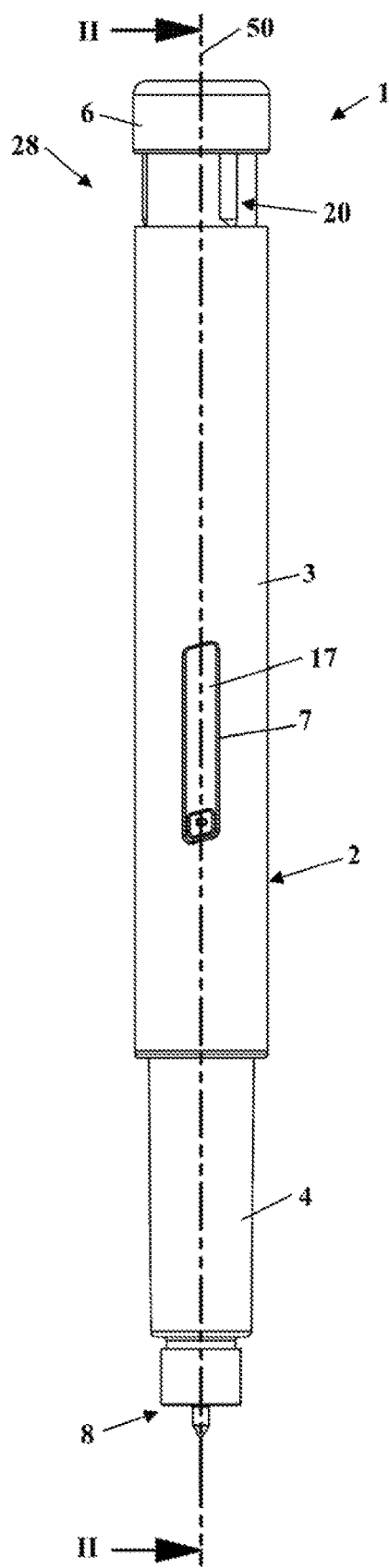
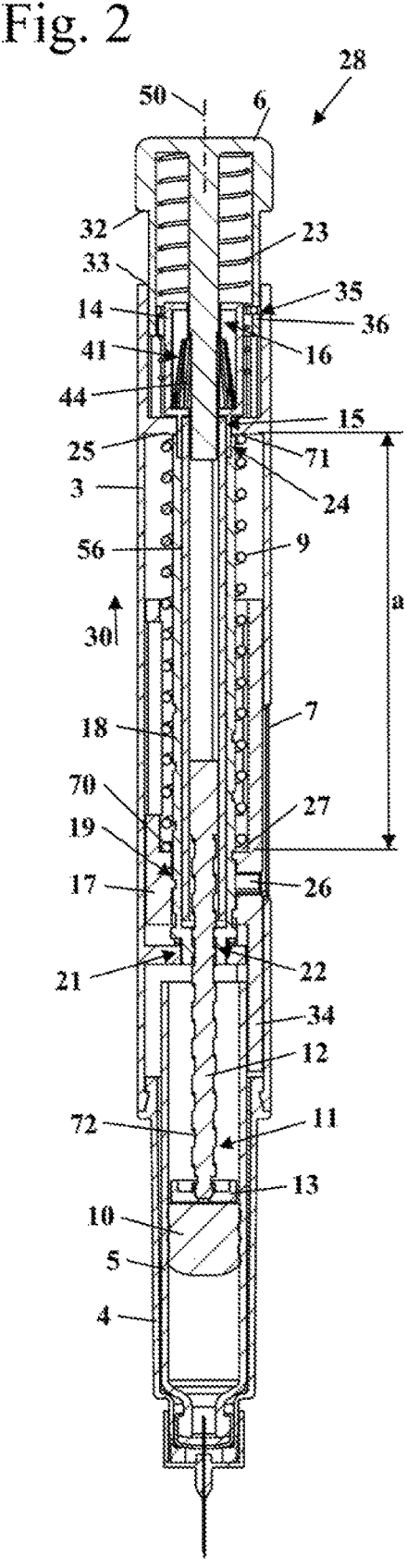

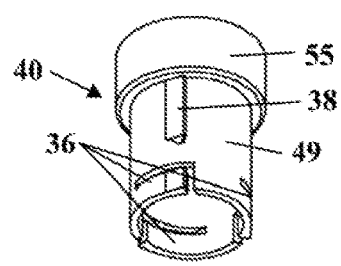
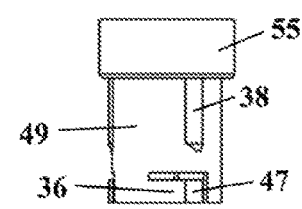

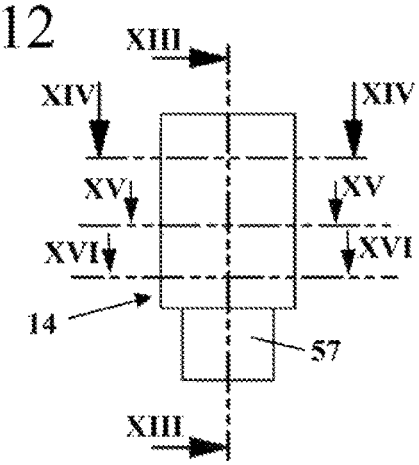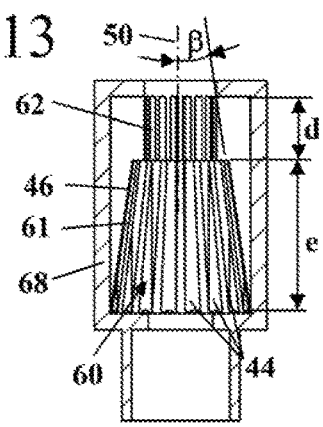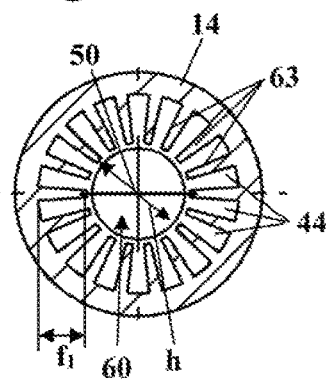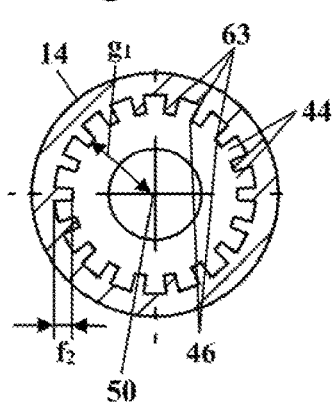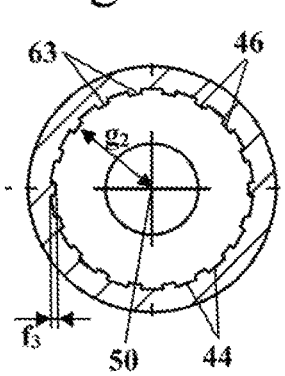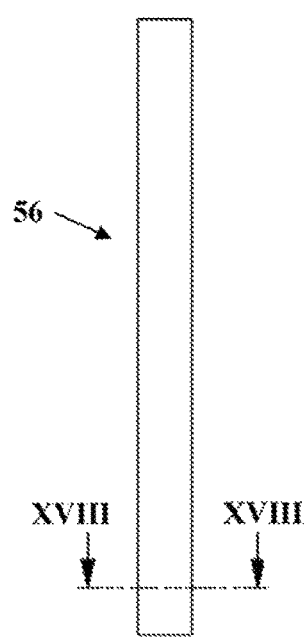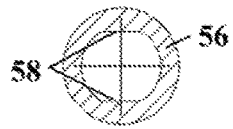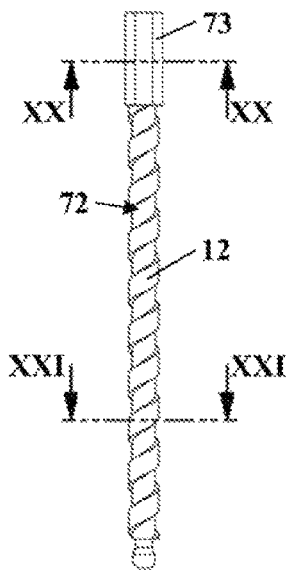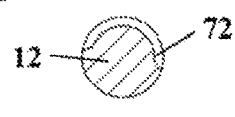

INJECTION DEVICE

CROSS REFERENCE TO RELATED APPLICATIONS

This application is a continuation application of international patent application PCT/EP2016/001598, filed Sep. 26, 2016, designating the United States and claiming priority from German application 20 2015 006 842.1, filed Sep. 30, 2015, and the entire content of both applications is incorporated herein by reference.

BACKGROUND OF THE INVENTION

An injection device in which the injection rate is settable is derived from WO 2014/166918 A1. The injection device has a drive part which rotates when squeezing out injection liquid and, on account thereof, moves a piston rod in the axial direction. A friction element which decelerates the drive part in the injection procedure is provided for setting the injection rate. The friction element is held in the housing of the injection device so as to be locationally fixed axially and in the circumferential direction. The injection rate is set by displacing the drive part in the axial direction.

SUMMARY OF THE INVENTION

It is an object of the invention to provide an injection device which has a simple construction and a reliable functionality.

This object can, for example, be achieved by an injection device for automatically squeezing out a dosage of injection liquid from a container thereof. The injection device includes: the container configured to hold the injection liquid; a housing defining a longitudinal central axis; a first component; a second component; wherein the first component and the second component move relative to one another when the injection liquid is squeezed out; an injection spring configured to store energy and to, when the injection liquid is squeezed out from the container, at least partially release the stored energy to cause the dosage of the injection liquid to be squeezed out from the container; a setting device to set an injection rate at which the injection liquid is squeezed out from the container; the setting device being configured to influence the energy required for moving the second component in relation to the first component; the first component, when squeezing out injection liquid, is guided in the housing so as to be movable in the direction of the longitudinal central axis and so as to be rotationally fixed; and, the second component, when squeezing out injection liquid, is mounted in relation to the housing so as to be rotatable and so as to be rotationally fixed in the direction of the longitudinal central axis.

The injection device has a setting device for setting the injection rate at which the injection liquid is squeezed out or pressed out from the container. On account thereof, the operator can set an injection rate that is comfortable for him/her and, for example, is adapted to the diameter of the needle used and to the viscosity of the liquid in the container. The setting device herein influences the energy that is required for moving the second component in relation to the first component. In the case of a high level of energy required, the injection is performed comparatively slowly, while the injection in the case of a low level of energy required is performed comparatively rapidly. In order for a simple construction of the injection device to be achieved, it is provided that the first component, when squeezing out injection liquid, is guided in the housing so as to be movable in the direction of the longitudinal central axis and so as to be rotationally fixed. On account thereof, the desired injection rate can be set in a simple manner by way of the axial position of the first component. The second component, when squeezing out injection liquid from the container, is mounted in relation to the housing so as to be rotatable and so as to be locationally fixed in the direction of the longitudinal central axis. The movements for setting the injection rate and for squeezing out the injection liquid, on account thereof, can be carried out by mutually separate movements of the first component and of the second component. A simple construction is achieved on account thereof.

The setting device advantageously enables a stepless setting of the injection rate. A particularly ergonomic handling results on account thereof. However, it can also be provided that the setting device predefines dissimilar rate stages that are settable. A simple construction combined with a small installation space of the setting device is achieved when the setting device, when setting the injection rate, acts on the axial relative position of the first component and the second component.

The setting device advantageously includes an operating element which is pretensioned by a setting spring. The setting spring herein counteracts a movement of the operating element in the direction toward an increase in the injection rate. The operating element, on account of the setting spring, during the injection is pushed in the direction toward the lowest settable injection rate. The lowest settable injection rate herein can also be a rate of 0. The force exerted by the setting spring has to be permanently overcome by the operator during the injection, in order for an injection rate to be achieved that is higher than the lowest settable injection rate. On account thereof, a dynamic setting of the injection rate is possible during the setting procedure. If the lowest settable injection rate is 0, the operator can interrupt the injection by releasing the operating element, and continue the injection by re-activating the operating element.

The operating element advantageously forms the first component and, for squeezing out injection liquid, is to be displaced in the proximal direction, counter to the force exerted by the setting spring. The setting spring herein preferably acts between the operating element and the housing. In an advantageous embodiment, the setting spring by way of one end is supported on the operating element, and by way of the other end is supported on the housing. On account of the setting spring acting directly between the operating element and the housing, and of the operating element being movable exclusively in the axial direction, the force required for setting the injection rate can be set in a precise and simple manner by a suitable layout of the setting spring.

In order for the energy which is required for moving the first component in relation to the second component to be influenced, a latching installation which acts between the first and the second component is advantageously provided. The latching installation herein advantageously influences the torque which is required for rotating the second component in relation to the first component. The latching installation herein, in a first relative position of the first component and the second component, requires a higher level of energy, in particular a higher torque, in order to overcome a latching mechanism than in a second relative position of the first component and the second component. However, it can also be provided that the setting device, additionally or alternatively to a latching installation, influences a friction force which acts between the first component and the second component. Comparatively great forces can be applied between the first component and the second component by way of the latching installation. On account thereof, the injection spring can be conceived so as to be comparatively strong such that a reliable squeezing out of injection liquid is achieved even in the case of a high viscosity of the liquid to be squeezed out and of a very thin needle used. In the case of a very low desired injection rate, a sufficiently great force can be generated between the first component and the second component such that a low injection rate is settable even in the case of an injection spring that is conceived so as to be strong.

A simple construction results when the latching installation includes at least one latching element which interacts with at least one counter latching element, wherein the latching depth by which the latching elements and the counter latching elements overlap is greater in the first relative position than in the second relative position. In order for a stepless adjustment of the setting device to be enabled, it is advantageously provided that the latching element in a sectional illustration which includes the longitudinal central axis has a latching edge that runs so as to be inclined in relation to the longitudinal central axis, and that the counter latching element has a counter latching edge that runs so as to be inclined in relation to the longitudinal central axis. The angles of inclination of the latching edge and of the counter latching edge herein are advantageously of equal size. The angles of inclination can be, for example, from 1° to 20°, in particular from 2° to 10°. The angles of inclination depend on the distance which the latching elements are to travel relative to one another between the lowest and the highest settable rate, and on the difference between the lowest and the highest rate. The angle of inclination also depends on the configuration of the latching installation, specifically on the geometry of the latching mechanism and on the rigidity of the materials used for the latching element and the counter latching element. The angle of inclination can be suitably chosen by means of the desired layout.

A simple construction results when the first latching element is configured as a latching web which protrudes into a latching depression that forms the counter latching element. In order for a uniform injection rate to be achieved, a multiplicity of latching elements and of counter latching elements are preferably provided. The number of latching elements that are configured as latching webs is advantageously higher than the number of latching depressions that are configured as counter latching elements.

The first component and the second component, when setting a quantity of injection liquid to be squeezed out, are advantageously interconnected in a rotationally fixed manner. The setting device, when setting a quantity of injection liquid to be squeezed out, in this instance can be disposed at any position, in particular at a position at which the setting device allows a free rotation of the components relative to one another. A simple construction results when at least one latching element of the latching installation is part of a coupling between the first component and the second component, the coupling connecting in a rotationally fixed manner the first component and the second component, when setting a quantity of injection liquid to be squeezed out. On account thereof, the at least one latching element, when setting the quantity of injection liquid to be squeezed out, serves for connecting the components in a rotationally fixed manner. When squeezing out or pressing out the quantity of injection liquid to be squeezed out, the latching element serves for setting the torque which in the case of a relative rotation counteracts the force of the injection spring between the first component and the second component.

A simple construction of the injection device results when the injection device has an injection sleeve which, when setting a dosage of injection liquid, moves in relation to the housing in the direction of the longitudinal central axis, and when the injection spring is configured as a compression coil spring which by way of a first end is supported in relation to the injection sleeve, and by way of a second end is supported in relation to the housing. The injection spring herein does not have to be supported directly on the injection sleeve or on the housing, but can also be supported on components which carry out a corresponding axial relative movement. The injection sleeve advantageously establishes the quantity of injection liquid to be squeezed out, wherein the injection sleeve for setting the quantity of injection liquid to be squeezed out is advantageously moved in the distal direction, and the proximal terminal position of the injection sleeve establishes the end of the injection.

BRIEF DESCRIPTION OF THE DRAWINGS

The invention will now be described with reference to the drawings wherein:

FIG. 1 shows a lateral view of an injection device in the zero position;

FIG. 2 shows a section along the line II-II in FIG. 1;

FIG. 12 shows a lateral view of an entrainment element of the injection device;

FIG. 13 shows a section along the line XIII-XIII in FIG. 12;

FIG. 14 shows a section along the line XIV-XIV in FIG. 12;

FIG. 15 shows a section along the line XV-XV in FIG. 12;

FIG. 16 shows a section along the line XVI-XVI in FIG. 12;

FIG. 17 shows a lateral view of a connection element of the injection device;

FIG. 18 shows a section along the line XVIII-XVIII in FIG. 17;

FIG. 19 shows a lateral view of a piston rod of the injection device;

FIG. 20 shows a section along the line XX-XX in FIG. 19;

FIG. 21 shows a section along the line XXI-XXI in FIG. 19;

DESCRIPTION OF THE PREFERRED EMBODIMENTS OF THE INVENTION

Figure 3:
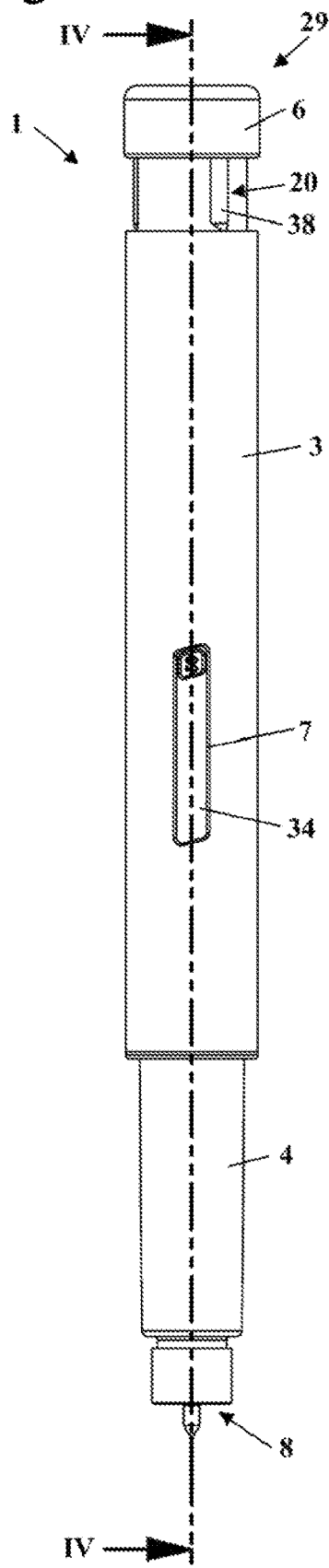
FIG. 3 shows a lateral view of the injection device from FIG. 1 in the maximum position.

FIG. 1 shows an injection device 1 as an embodiment of a mechanical injection device in which the squeezing out of a dosage of injection liquid is performed automatically. The injection device 1 has a housing 2 which includes an upper housing part 3 and a holder 4 which is secured on the upper housing part 3. The holder 4 is disposed on the proximal side of the upper housing part 3. An injection needle 8 is secured on the proximal side of the holder 4. An operating element 6 is disposed on the distal side of the injection device 1. The operating element 6 by way of a coupling 20 is connectable in a rotationally fixed manner to the upper housing part 3. The upper housing part 3 has a viewing window 7 which is advantageously composed of a transparent material such that an injection sleeve 17 that is disposed in the upper housing part 3 is visible through the viewing window 7. The injection device 1 has a longitudinal central axis 50 which runs in the longitudinal direction of the injection device 1.

The distal end of the injection device 1 is that end that faces away from an injection needle 8 that is held on the injection device. "Proximal" refers to that side of the injection device 1 which in an injection faces the pierced location, and "distal" refers to that side that faces away from the pierced location. The proximal direction describes the injection direction, thus the direction toward the injection needle 8, or the direction in which the injection liquid is squeezed out from a container. The distal direction describes the opposite direction, thus away from the injection needle 8.

FIGS. 1 and 2 show the injection device 1 in a zero position 28 at which no dosage of injection liquid is set. As is shown in FIG. 2, a container 5 having an injection liquid is disposed in the holder 4. A plug 10 is disposed in the container 5, a piston disk 13 of a metering piston 11 bearing on the plug 10. The metering piston 11 moreover includes a piston rod 12 which supports an external thread 72.

The external side of the injection sleeve 17 is visible through the viewing window 7 of the upper housing part 3. The injection sleeve 17 has an opening 26 through which the external circumference of a metering member 18 that is disposed within the injection sleeve 17 is visible. The metering member 18 which can also be referred to as a graduated tube, on the external circumference thereof supports a scale 59 (shown in FIG. 30) which is visible to the operator through the viewing window 7 and through the opening 26, and displays the set dosage of injection liquid to be squeezed out.

The injection sleeve 17 is held in the upper housing part 3 so as to be displaceable in the direction of the longitudinal central axis 50 and so as to be rotationally fixed in relation to the upper housing part 3. The metering member 18 and the injection sleeve 17 are interconnected by way of a first threaded connection 19. The metering member 18 is mounted on a pivot bearing 21 so as to be rotatable and axially non-displaceable on the upper housing part 3. The metering member 18 by way of a second threaded connection 22 is connected to the external thread 72 of the piston rod 12.

An entrainment element 14 is mounted in the upper housing part 3. The entrainment element 14 is connected in a rotationally fixed manner to the metering member 18 by way of a rotationally fixed connection 24. The rotationally fixed connection 24 can be a press-fit connection. However, it can also be provided that the rotationally fixed connection 24 is a form-fitting connection. The entrainment element 14 is mounted so as to be rotatable on a pivot bearing 15 that is configured in an upper housing part 3 and in a locationally fixed manner in the direction of the longitudinal central axis 50. The pivot bearing 15 is formed by a periphery of the upper housing part 3. In the context of the usual production tolerances, the entrainment element 14 herein in the direction of the longitudinal central axis 50 can be movable in relation to the upper housing part 3.

As is also shown in FIG. 2, an injection spring 9, which is configured as a compression coil spring, is disposed in the upper housing part 3. The injection spring 9 by way of a first end 70 is supported on a bearing periphery 27 of the injection sleeve 17, and by way of a second end 71 is supported on a bearing periphery 25 of the upper housing part 3. The pivot bearing 15 for the entrainment element 14 is also configured on the bearing periphery 25.

The operating element 6 is connected in a rotationally fixed manner to the piston rod 12 by way of a connection element 56 which is configured as a sleeve. The operating element 6 is supported in relation to the upper housing part 3 by way of a setting spring 23 which is configured as a compression coil spring. The setting spring 23 herein, by way of one distal end thereof, is supported on the operating element 6, and by way of the other proximal end thereof, is supported on the periphery 25 of the upper housing part 3. The setting spring 23, which pushes the operating element 6 in the distal direction, has no influence on the injection rate. The setting spring 23 is conceived merely such that the operator can activate the operating element 6 by way of a comfortable force. A shoulder 32 which, in the case of an operating element 6 that is pushed in the proximal direction, interacts with a periphery 33 of the upper housing part 3 is configured on the operating element 6, the shoulder 32 conjointly with the periphery 33 forming a detent which delimits the proximal position of the operating element 6. A latching installation 35 which includes a plurality of latching arms 36, one of which being visible in FIG. 2, acts between the operating element 6 and the upper housing part 3. The operating element 6 in the zero position 28 shown in FIGS. 1 and 2 is coupled in a rotationally fixed manner to the entrainment element 14 by way of a coupling 16. Moreover, a setting device 41 which includes a multiplicity of latching depressions 44 in the entrainment element 14 is formed between the operating element 6 and the entrainment element 14.

In the case of a non-activated operating element 6, the setting spring 23 pushes the operating element 6 to the distal position thereof, in which the coupling 20 is opened and the operating element 6 is rotatable in relation to the housing 2. In order to set a quantity of injection liquid to be squeezed out, the operator rotates the operating element 6 about the longitudinal central axis 50. The entrainment element 14 that by way of the coupling 16 is connected in a rotationally fixed manner to the operating element 6 is conjointly rotated herein. The entrainment element 14 by way of the rotationally fixed connection 24 is connected to the metering member 18 which is likewise conjointly rotated. The piston rod 12 by way of the connection element 56 is connected in a rotationally fixed manner to the operating element 6 and is likewise conjointly rotated. The injection sleeve 17, by virtue of the first threaded connection 19 and of the fixing of the injection sleeve 17 in a rotationally fixed manner in the upper housing part 3, is moved in a distal direction 30 in the rotating movement of the metering member 18. The bearing periphery 27 herein moves toward the bearing periphery 25 of the injection spring 9, on account of which the injection spring 9 is tensioned.

Figure 4:
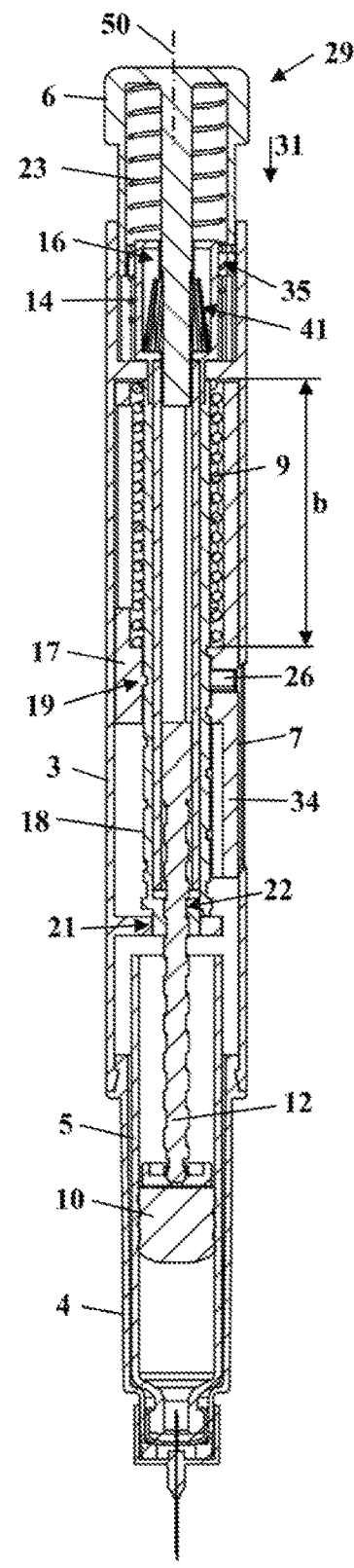
FIG. 4 shows a section along the line IV-IV in FIG. 1.

FIGS. 3 and 4 show the injection device 1 in a maximum position 29 at which the maximum dosage is set. The length of the injection spring 9 has been shortened from the largely relaxed length a, shown in FIG. 2, to the tensioned length b, shown in FIG. 4. The injection spring 9 is at least slightly pretensioned also in the zero position 28, such that the injection liquid can be completely squeezed out. As is shown in FIG. 3, the maximum dosage is visible through the viewing window 7 in the maximum position 29. The injection sleeve 17 has a web 34 which protrudes in the proximal direction and covers the region of the metering member 18 that is visible through the viewing window 7 and that does not display the set dosage.

Figure 38:
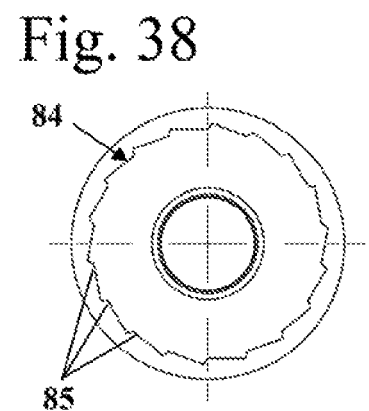
FIG. 38 shows a lateral view in the direction of the arrow XXXVIII in FIG. 36.

In order for a set quantity of injection liquid to be squeezed out, the operator pushes the operating element 6 counter to the force of the setting spring 23 in a proximal direction 31. On account thereof, webs 38 of the coupling 20 (FIG. 1) come to engage with latching elements 85 of the latching installation 35 (FIG. 38). On account thereof, the operating element 6 in relation to the upper housing part 3 is fixed in a rotationally fixed manner. At the same time, the coupling 16 by virtue of the axial relative movement of the operating element 6 in relation to the entrainment element 14 is at least partially released such that the entrainment element 14, conjointly with the metering member 18, can rotate about the longitudinal central axis 50. The rotating movement is performed by virtue of the axial force that is exerted by the tensioned injection spring 9 on the injection sleeve 17, the force causing a rotation of the metering member 18. The rotation is performed by virtue of the threaded connection 19 and of the injection sleeve 17 being guided in a rotationally fixed manner in the housing part 3. The piston rod 12 is connected in a rotationally fixed manner to the upper housing part 3 by way of the connection element 56 and of the operating element 6. Therefore, the second threaded connection 22 in the rotation of the metering member 18 causes a movement of the piston rod 12 in the proximal direction 31. On account thereof, the set quantity of injection liquid is squeezed out.

By virtue of the force stored in the injection spring 9, the injection is performed automatically upon releasing the coupling 16. The injection device 1 has the setting device 41 in order for the injection rate to be set. The setting device 41 influences the energy, specifically the torque that is required for rotating the entrainment element 14 in relation to the operating element 6. The torque required herein depends on the axial position of the operating element 6 in relation to the upper housing part 3 and to the entrainment element 14. This will be explained in yet more detail hereunder.

Figure 8:
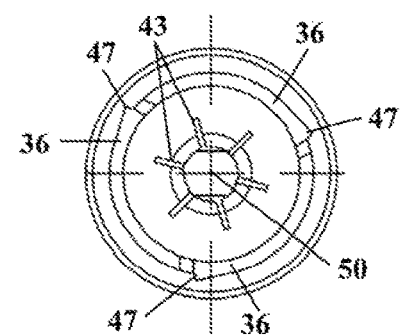
FIG. 8 shows a view of the operating element in the direction of the arrow VIII in FIG. 6.

FIGS. 5 to 11 show the construction of the operating element 6 in detail. The operating element 6 has an operating portion 55 which protrudes from the upper housing part 3, the operator being able to rotate the operating element 6 or to displace the latter in the proximal direction 31 at the operating portion 55. The operating element 6 has a sleeve portion 49 (shown in FIGS. 5 and 6) which in the zero position 28 and the maximum position 29 protrudes partially from the upper housing part 3, the webs 38 of the coupling 20 being fixed to the sleeve portion 49. The sleeve portion 49 on the proximal end thereof supports a total of three latching arms 36 which at the free end thereof have in each case one latching element 47. This is also shown in FIG. 8. The outwardly protruding latching elements 47 by way of the latching arms 36 are mounted so as to be movable in a radially inward manner.

Figure 5:
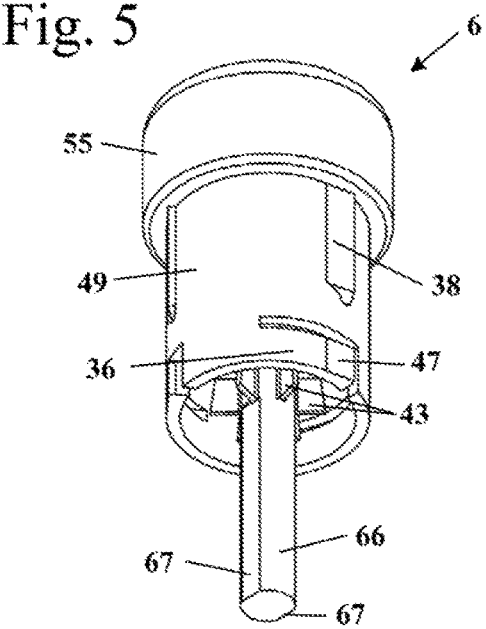
FIG. 5 shows a perspective illustration of the operating element of the injection device from FIGS. 1 to 4.
Figure 6:
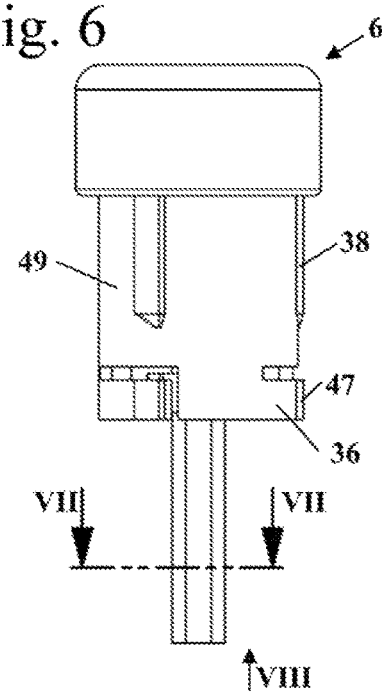
FIG. 6 shows a lateral view of the operating element from FIG. 5.
Figure 7:
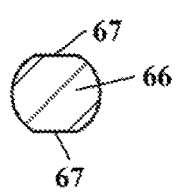
FIG. 7 shows a section along the line VII-VII in FIG. 6.

As is also shown in FIG. 5, the operating element 6 has a connector 66 which on the external circumference thereof supports two bevels 67 for connecting in a rotationally fixed manner to the connection element 56. As is shown in FIGS. 17 and 18, the connection element 56, which is configured so as to be sleeve-shaped, on the internal side thereof has corresponding bevels 58 which interact with the bevels 67 of the connector 66 and, on account thereof, interconnect in a rotationally fixed manner the operating element 6 and the connection element 56. As is shown in FIGS. 19 and 20, the piston rod 12 on a distal end portion 73 supports corresponding bevels 74 in order for the piston rod 12 and the connection element 56 to be connected in a rotationally fixed manner. The external thread 72 of the piston rod 12 is also shown in FIGS. 19 and 21.

Figure 9:
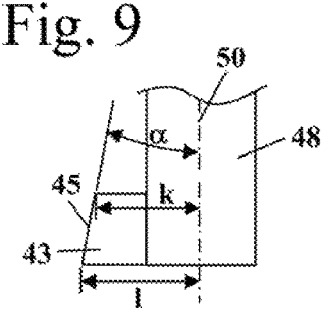
FIG. 9 shows a schematic illustration of a latching web of the operating element.
Figure 25:
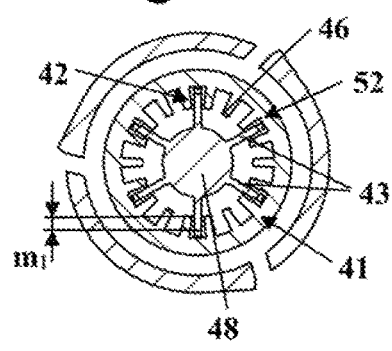
FIG. 25 shows a section along the line XXV-XXV in FIG. 24.

As is shown in FIGS. 5 and 8, the operating element 6 in the embodiment has six latching webs 43 which conjointly with the latching depressions 44 of the entrainment element 14 form a latching installation 42 (FIG. 25). The latching webs 43 in the embodiment are configured as ribs of an approximately constant thickness which in relation to the longitudinal central axis 50 protrude radially outward. The thickness of the latching webs 43 herein is significantly smaller than the radial extent. As is schematically shown in FIG. 9, each latching web 43 has a radially outward latching edge 45. The latching edges 45 are inclined in relation to the longitudinal central axis 50 by an angle α. In the embodiment shown, the angle α is 1° to 20°, in particular 2° to 10°. The angle α is adapted to the desired activation distance between the slowest and the fastest injection rate that can be set, and to the desired difference between the slowest and the fastest injection rate. The latching web 43, on the proximal side thereof, has a spacing l from the longitudinal central axis 50 which is significantly larger than the spacing k of the latching edge 45 on the distal side of the latching web 43. The difference between the spacings k and l is suitably selected depending on the desired layout.

As is schematically shown in FIG. 9, the latching webs 43 are disposed on a pin portion 48 of the operating element 6, the pin portion 48 running within the sleeve portion 49 at a radial spacing from the sleeve portion 49. The connector 66 adjoins the pin portion 48 at the proximal end. The latching webs 43 in the embodiment are configured so as to be integral to the operating element 6 and are composed of the same material as the operating element 6. However, it can also be advantageous for the latching webs 43 to be configured from another material, for example from an elastomer or a rubber, in order for a desired latching characteristic to be set.

Figure 10:
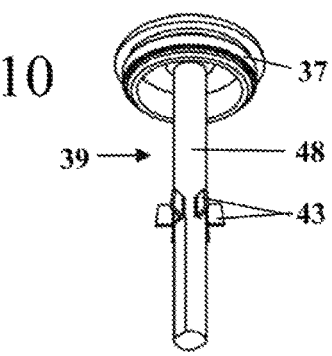
FIG. 10 shows a schematic perspective illustration of the operating element in two individual parts.
Figure 11:
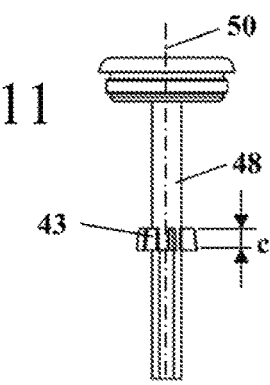
FIG. 11 shows a lateral view of the two individual parts of the operating element.

As is shown in FIGS. 10 and 11, the operating element 6 is constructed from a first individual part 39 and from a second individual part 40, in order for the production and the assembly to be simplified. The operating element 6 can also be formed from a larger number of individual parts. The individual parts 39 and 40 in the embodiment are fixedly interconnected at a latching periphery 37 of the first individual part 39.

FIGS. 12 to 16 show the configuration of the entrainment element 14 in detail. The entrainment element 14 has a bearing portion 57 having a reduced diameter, by way of which the entrainment element 14 is rotatably mounted in the upper housing part 3. As is shown in FIG. 13, the entrainment element 14 in the interior thereof has a conical portion 61 which is disposed in a proximal region, a cylindrical portion 62 adjoining the conical portion 61 on the distal side of the latter. The conical portion 61 and the cylindrical portion 62 are formed by a multiplicity of webs 63 (shown in FIGS. 14 to 16) which protrude in a radially inward manner from a cylindrical external wall 68 of the entrainment element 14. The latching depressions 44 are formed in the circumferential direction between the webs 63. The webs 63 have radially inward counter latching edges 46 which are inclined in relation to the longitudinal central axis 50 by an angle $\beta$. The angle $\beta$ herein is open toward the proximal direction. In particular, the angle $\beta$ is the same size as the angle $\beta$ of the latching edges 45 of the latching webs 43. In the assembled state of the injection device 1, the latching webs 43 are within the entrainment element 14, in the embodiment within the space that is enclosed by the cylindrical external wall 68.

As is shown in FIG. 11, the latching webs 43 have a measured height c in the direction of the longitudinal central axis 50. The cylindrical portion 62 has a height d, which is slightly greater than the height c in the embodiment. The webs 63 in the cylindrical portion 62 delimit an interior space 60, the interior diameter h of the latter (shown in FIG. 14) being only slightly larger than the external diameter of the pin portion 48. The webs 63 in the radial portion 62 have a radially measured height $f_1$ that corresponds to approximately the radial extent of the latching webs 43.

FIG. 15 shows a section through the conical portion 61. The radially inward latching edges 46 of the webs 63 in the section plane shown in FIG. 15 have a spacing $g_1$ from the longitudinal central axis 50 which is smaller than the spacing I of the latching edge 45 from the longitudinal central axis 50 (FIG. 9). If the proximal side of the latching webs 43 is located in the sectional plane shown in FIG. 15, the latching webs 43 protrude into the latching depressions 44. The radially measured height $f_2$ of the webs 63 in the section plane through the conical portion 61 shown in FIG. 15 is significantly smaller than the height $f_1$ in the cylindrical portion 62.

FIG. 16 shows a section through the conical portion 61, adjacent to the proximal end of the interior space 60. The latching edges 46 in this section plane have a spacing $g_2$ from the longitudinal central axis 50 which is significantly larger than the spacing $g_1$. The spacing $g_2$ can correspond to approximately the spacing I of the latching edge 45 from the longitudinal central axis 50. If the proximal side of the latching webs 43 is located in the sectional plane shown in FIG. 16, the latching webs 43, if at all, engage only slightly between the webs 63. The radially measured height $f_3$ of the webs 63 in the section plane through the conical portion 61 shown in FIG. 15 is significantly smaller than the height $f_2$ in the distal section plane shown in FIG. 15.

Figure 22:
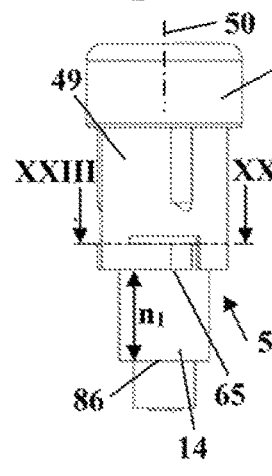
FIG. 22 shows a lateral view of the operating element and of the entrainment element in a coupling position.
Figure 23:
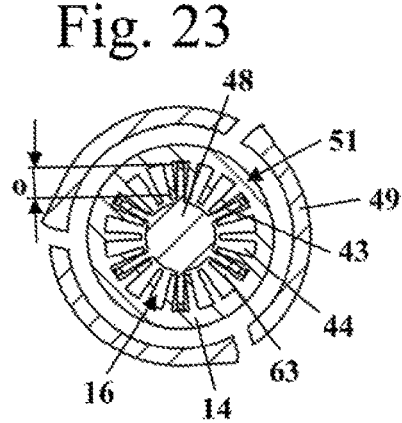
FIG. 23 shows a section along the line XXIII-XXIII in FIG. 22.

FIGS. 22 to 29 show the operating element 6 and the entrainment element 14 in different axial relative positions. FIGS. 22 and 23 show the operating element 6 and the entrainment element 14 in a coupling position 51. In this position, the operating element 6 and the entrainment element 14 are interconnected in a rotationally fixed manner by way of the coupling 16. The operating element 6 is pretensioned in this position by the setting spring 23. The coupling 16 is formed by the webs 63 in the cylindrical portion 62. The webs 63 protrude up to short of the pin portion 48 and overlap the webs 63 on the distal side thereof in the circumferential direction by an engagement depth o. The engagement depth o is chosen such that the entrainment element 14 and the operating element 6 are interconnected in a rotationally fixed manner. FIGS. 23, 25, 27, and 29 herein show sections through the operating element 6 on the distal side of the latching webs 43. The sleeve portion 49 has a proximal end side 65. The proximal end side 65 in the coupling position 51 has a first spacing $n_1$, measured from a lower edge 86 of the entrainment element 14 in the direction of the longitudinal central axis 50. The lower edge 86 herein is that edge of the entrainment element 14 that bears on the inwardly protruding periphery of the upper housing part 3.

Figure 24:
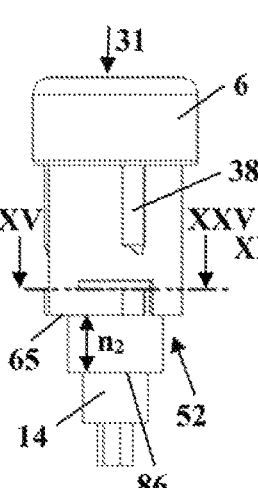
FIG. 24 shows a lateral view of the operating element and of the entrainment element in a first relative position.

FIGS. 24 and 25 show the operating element 6 and the entrainment element 14 in a first relative position 52, at which the setting device 41 acts between the operating element 6 and the entrainment element 14. The proximal end side 65 of the sleeve portion 49 has a spacing $n_2$ from the lower edge 86 of the entrainment element 14 which is smaller than the spacing $n_1$. As is shown in FIG. 25, the latching webs 43 are in the conical portion 61 in which the spacing of the latching edges 46 of the webs 63 from the pin portion 48 and from the longitudinal central axis 50 is reduced. In this relative position, the latching webs 43, on the distal side of the latching webs 43, overlap the webs 63 in the radial direction by a latching depth $m_1$. The latching depth $m_1$ is significantly smaller than the engagement depth o in the coupling position 51. The latching depth $m_1$ is chosen such that the entrainment element 14 can rotate in relation to the operating element 6 while deforming the latching webs 43.

In order to reach the first relative position 52 from the coupling position 51, the operator has to move the operating element 6 in the proximal direction 31 counter to the force of the setting spring 23, as is indicated in FIG. 24. On account thereof, the operating element 6 is displaced relative to the upper housing part 3, and the webs 38 on the operating element 6 come to engage with a latching mechanism 84 (shown in FIGS. 36 and 38) on the internal side of the upper housing part 3. The latching mechanism 84 has a multiplicity of latching elements 85 which secure the operating element 6 in a rotationally fixed manner in relation to the external housing part 3. The webs 38, conjointly with the latching mechanism 84, form the coupling 20.

In the case of the first relative position 52, shown in FIGS. 24 and 25, the entrainment element 14 can rotate relative to the upper housing part 3 and relative to the operating element 6 when the energy stored in the injection spring 9 is sufficient in order for the latching webs 43 to be deformed and for the plug 10 to slide in the proximal direction such that the injection liquid is squeezed out from the container 5. However, by virtue of the high torque that is required for rotating the entrainment element 14 in relation to the operating element 6, the squeezing out of injection liquid is performed very slowly. The energy which is required for rotating the entrainment element 14 in relation to the operating element 6 is large.

Figure 26:
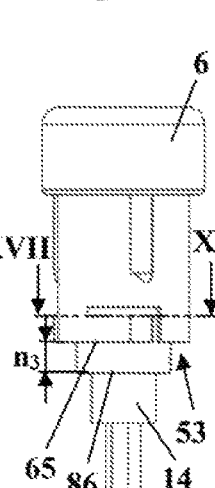
FIG. 26 shows a lateral view of the operating element and of the entrainment element in a second relative position.
Figure 27:
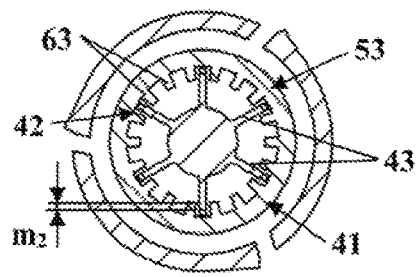
FIG. 27 shows a section along the line XXVII-XXVII in FIG. 26.

In the second relative position 53, shown in FIGS. 26 and 27, of the operating element 6 and of the entrainment element 14, the operator has pushed the operating element 6 in the proximal direction 31 further into the upper housing part 3 counter to the force of the setting spring 23. The proximal end side 65 in this position has a third spacing $m_3$ from the lower edge 86 of the entrainment element 14. The third spacing $m_3$ is significantly smaller than the second spacing $m_2$. In the movement of the operating element 6 in the proximal direction 31 the latching webs 43 in the conical portion 61 have moved further in the proximal direction, thus in the direction toward an enlarged internal diameter of the conical portion 61. The distal side of the latching webs 43 in the radial direction toward the longitudinal central axis 50 has a minor overlap in relation to the webs 63, such that only a minor latching depth $m_2$ results. In this position of the setting device 41, the torque required for rotating the entrainment element 14 in relation to the operating element 6 is significantly smaller than in the case of the first relative position 52 shown in FIGS. 24 and 25. The energy which is required for rotating the entrainment element 14 in relation to the operating element 6 is smaller than in the first relative position 52. The latching webs 43 have to be only slightly deformed in order for the webs 63 to be overcome and for the next latching position to be reached. On account thereof, an injection at the second relative position shown in FIGS. 26 and 27 is performed at a higher rate than in the case of the first relative position shown in FIGS. 24 and 25.

Figure 28:
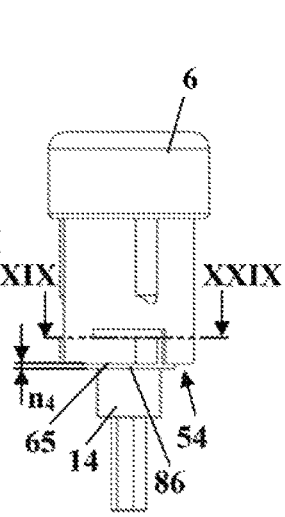
FIG. 28 shows a lateral view of the operating element and of the entrainment element in a third relative position.
Figure 29:
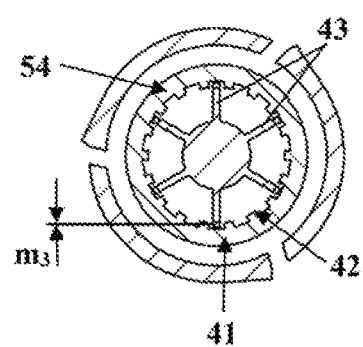
FIG. 29 shows a section along the line XIX-XIX in FIG. 28.

FIGS. 28 and 29 show the operating element 6 and the entrainment element 14 in a third relative position 54 in which the lower edge 86 has only a very minor fourth spacing n4 from the proximal end side 65. The operating element 6 is in the proximal terminal position thereof in the third relative position 54, in which the shoulder 32 (shown in FIG. 2) bears on the periphery 33 of the upper housing part 3. As is shown in FIG. 29, the latching webs 43 in the third relative position 54 in the radial direction have an extremely minor overlap in relation to the webs 63. The latching depth $m_3$ is minimal. It can also be provided that the latching depth $m_3$ is zero, such that the latching webs 43 can freely rotate in relation to the webs 63, and the setting device 41 in the third relative position 54 does not slow down the rotation of the entrainment element 14 in relation to the operating element 6. Therefore, the highest possible injection rate results in the third relative position 54. The energy which is required for rotating the entrainment element 14 in relation to the operating element 6 is minor. The injection rate is determined by the force stored in the injection spring 9 and by the friction forces which act between the mutually moving components.

The setting spring 23 in the injection procedure acts in the distal direction on the operating element 6. In order for the injection rate to be maintained, the operator has to permanently push on the operating element 6. If the operator decreases or increases the pressure on the operating element 6, the operating element 6 correspondingly moves in the direction of the longitudinal central axis 50, and the injection rate changes. On account thereof, a dynamic setting of the injection rate is possible during the injection procedure. If the operating element 6 is released, the setting spring 23 resets the operating element 6 to the coupling position 51, and the injection procedure is stopped. The injection procedure can be continued by pushing the operating element 6 again.

The angle α of the latching edge 45 of the latching web 43 and the angle β of the latching edge 46 of the web 63 are identical in the embodiment. On account thereof, the latching depths $m_1$, $m_2$, $m_3$ are the same across the entire height c of the latching webs 43. In the case of dissimilar angles α, β, dissimilar latching depths m result in different portions of the latching web 43. The force exerted by the setting device 41 can be influenced by a suitable choice in terms of the configuration and the number of the latching webs 43.

Figure 30:
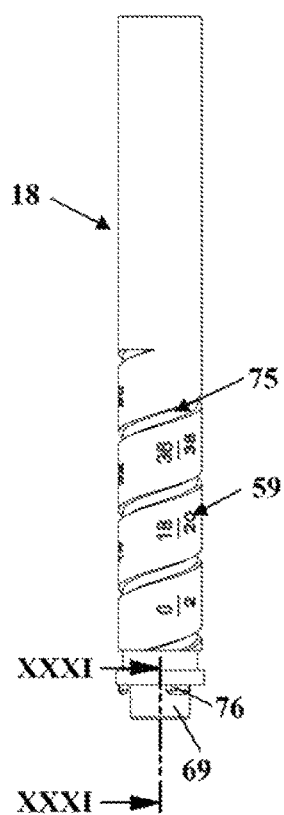
FIG. 30 shows a lateral view of a metering member of the injection device.
Figure 31:
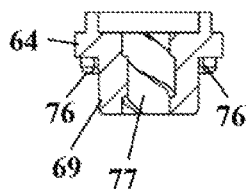
FIG. 31 shows a section along the line XXXI-XXXI in FIG. 30.
Figure 36:
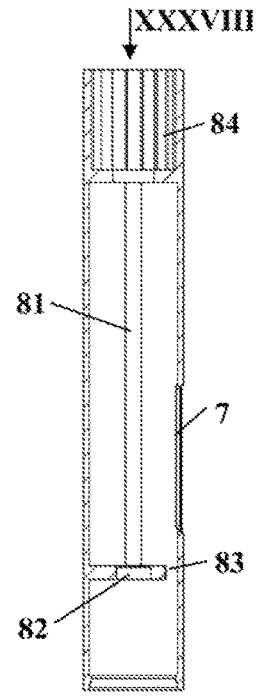
FIG. 36 shows a section along the line XXXVI-XXXVI in FIG. 35.
Figure 37:
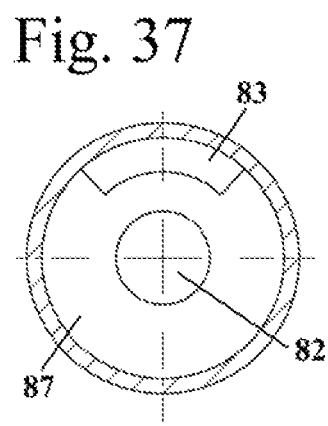
FIG. 37 shows a section along the line XXXVII-XXXVII in FIG. 35.

FIGS. 30 and 31 show the metering member 18 in detail. The metering member 18 has an external thread 75 which, conjointly with an internal thread 80 of the injection sleeve 17 (shown in FIG. 34), forms the first threaded connection 19. The metering member 18 has a bearing connector 69 by way of which the metering member 18 is rotatably mounted in a bearing opening 82 in the upper housing part 3 (FIGS. 36 and 37). The metering member 18 has bearing webs 76 which bear on a distal side of a housing wall 87 that has the bearing opening 82. The friction between the metering member 18 and the upper housing part 3 in the rotating movement of the metering member 18 is reduced. The bearing webs 76 are disposed on a periphery 64 that protrudes outward from a bearing connector 69. The distal side of the periphery 64 forms a detent for the proximal terminal position of the injection sleeve 17 and thus limits the quantity of injection liquid to be squeezed out. Alternatively, the detent for the proximal terminal position of the injection sleeve 17 can also be formed on the distal face of the housing wall 87 (FIG. 37) of the upper housing part 3. Another configuration of the detent can also be advantageous. As is shown in FIG. 31, an internal thread 77 which, conjointly with the external thread 72 of the piston rod 12, forms the second threaded connection 22 is configured in the bearing connector 69 (FIG. 2).

Figure 32:
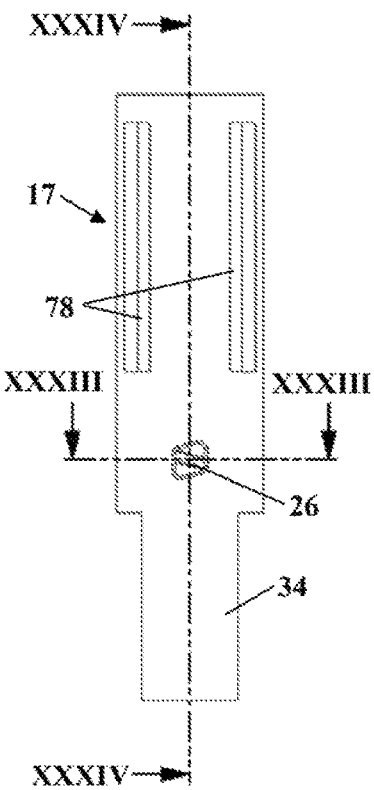
FIG. 32 shows a lateral view of an injection sleeve of the injection device.
Figure 33:
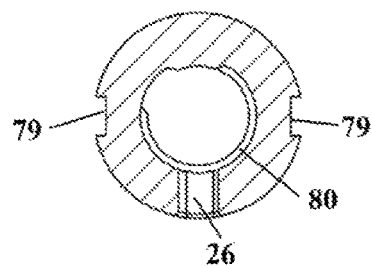
FIG. 33 shows a section along the line XXXIII-XXXIII in FIG. 32.
Figure 34:
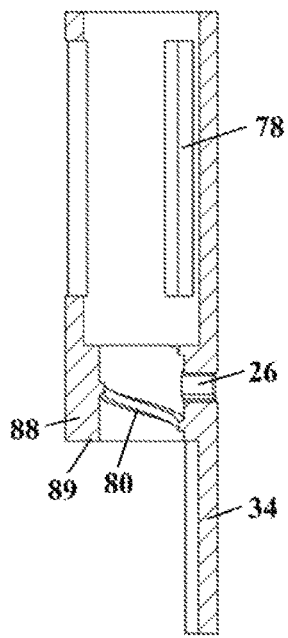
FIG. 34 shows a section along the line XXXIV-XXXIV in FIG. 32.
Figure 35:
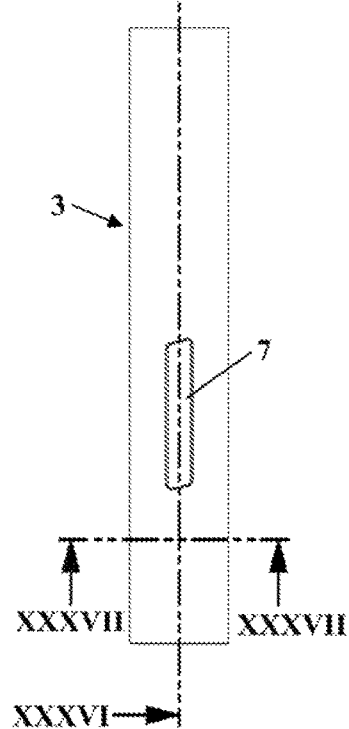
FIG. 35 shows a lateral view of an upper housing part of the injection device.

As is shown in FIG. 32, the injection sleeve 17 has clearances 78 which serve for reducing the weight. The opening 26 behind which the scale 59 of the metering member 18 (FIG. 30) is visible to the operator is also shown in FIGS. 32 to 34.

The injection sleeve 17 on the external circumference thereof has two guide grooves 79 which are disposed so as to be mutually opposite. Corresponding guide webs 81, one of which being visible in FIG. 36, are configured in the upper housing part 3. The guide webs 81 protrude into the guide grooves 79 and, on account thereof, guide in a rotationally fixed manner the injection sleeve 17 in the upper housing part 3 so as to be movable in the direction of the longitudinal axis 50. A portion 88 of the injection sleeve 17 that has the internal thread 80 has a proximal end side 89 which in the proximal terminal position of the injection sleeve 17 bears on the periphery 64 of the metering member 18 and conjointly with the latter forms a detent for the proximal terminal position of the injection sleeve 17.

As is shown in FIG. 37, the housing wall 87 beside the bearing opening 82 has a passage opening 83, the web 34 of the injection sleeve 17 protruding through the latter. On account of the web 34, a small construction length of the injection device 1 is achieved at a sufficiently large adjustment range of the metering member 18. The metering member 18 rotates and the injection sleeve 17 is displaced in the axial direction when the dosage is being set. On account thereof, the set dosage is in each case visible through the opening 26.

As is shown in FIG. 38, the latching elements 85 of the latching mechanism 84 in the embodiment are configured so as to be non-symmetrical. The latching elements 85 interact with the latching elements 47 on the operating element 6 (FIG. 5). A dosage once set cannot be reduced by virtue of the non-symmetrical configuration of the latching elements. However, a reverse rotation of the operating element 6 for reducing a set dosage can also be possible by way of a corresponding configuration of the latching elements 85 and of the latching elements 47.

Clicking noises on account of the latching elements 47 and 85 are audible when setting a quantity of injection liquid to be squeezed out. As the operating element 6 and the upper housing part 3 are interconnected in a rotationally fixed manner when a quantity of injection liquid is being squeezed out, the clicking noises of the latching installation 35 are not audible when squeezing out injection liquid. Instead, clicking noises of the latching installation 42 of the setting device 41 are audible to the operator when squeezing out injection liquid. The latching installation 42 in the first latching position 52 herein generates louder clicking noises at a larger temporal interval. The further the operating element 6 is pushed in the proximal direction 31, the quieter the clicking noises and the more rapid the succession of the clicking noises. On account thereof, the injection rate is audible to the operator. The latching elements 85, conjointly with the latching elements 47, form the latching installation 35 when setting the dosage of injection liquid to be squeezed out. In the squeezing out of injection liquid, the latching elements 85 interact with the webs 38 and, conjointly with the latter, form the coupling 20 and connect the operating element 6 in a rotationally fixed manner to the upper housing part 3.

Another constructive configuration can also be expedient for the setting device 41. A stepless setting of the injection rate is possible by way of the setting device 41 on account of the conical portion 61. However, it can also be expedient for different steps to be predefined for the setting of the injection rate, for example by way of a correspondingly stepped profile of the latching edge 46. It can be provided that latching positions for the operating element 6 are predefined for the individual injection rates to be set. The setting device 41 shown can also be provided for injection devices which have another constructive layout and provide an automatic injection.

It is understood that the foregoing description is that of the preferred embodiments of the invention and that various changes and modifications may be made thereto without departing from the spirit and scope of the invention as defined in the appended claims.

What is claimed is:

1. An injection device for automatically squeezing out a dosage of injection liquid from a container thereof, the injection device comprising:
said container configured to hold the injection liquid;
a housing defining a longitudinal central axis;
a first component;
a second component;
wherein said first component and said second component move relative to one another when the injection liquid is squeezed out;
an injection spring configured to store energy and to, when the injection liquid is squeezed out from said container, at least partially release said stored energy to cause the dosage of the injection liquid to be squeezed out from said container;
a setting device to set an injection rate at which the injection liquid is squeezed out from said container;
said setting device comprising a latching installation which acts between said first component and said second component and being configured to influence an energy required for moving said second component in relation to said first component, wherein said latching installation, in a first relative position of said first component and said second component, has a greater force for overcoming latching than in a second relative position of said first component and said second component;
said first component, when squeezing out the injection liquid, is guided in said housing so as to be movable in the direction of said longitudinal central axis and so as to be rotationally fixed;
said second component, when squeezing out the injection liquid, is mounted in relation to said housing so as to be rotatable and so as to be rotationally fixed in the direction of said longitudinal central axis.

2. The injection device of claim 1, wherein said setting device enables a stepless setting of said injection rate.

3. The injection device of claim 1, wherein said setting device, when setting the injection rate, acts on an axial relative position of said first component and said second component.

4. The injection device of claim 1, wherein:
said latching installation includes at least one latching element which interacts with at least one counter latching element;
said at least one latching element and said at least one counter latching element conjointly define a latching depth with which said at least one latching element and said at least one counter latching element overlap; and,
said latching depth is greater in a first relative rotary position than in a second relative rotary position.

5. The injection device of claim 4, wherein:
said at least one latching element, in a sectional view which includes said longitudinal central axis, has a latching edge;
said latching edge runs so as to be inclined in relation to said longitudinal central axis;
said at least one counter latching element has a counter latching edge; and,
said counter latching edge runs so as to be inclined in relation to said longitudinal central axis.

6. The injection device of claim 5, wherein:
at least one of said at least one latching element of said latching installation is part of a coupling between said first component and said second component; and,
said coupling connects said first component and said second component in a rotationally fixed manner when setting a quantity of injection liquid to be squeezed out.

7. The injection device of claim 4, wherein:
at least one of said at least one latching element of said latching installation is part of a coupling between said first component and said second component; and,
said coupling connects said first component and said second component in a rotationally fixed manner when setting a quantity of injection liquid to be squeezed out.

8. The injection device of claim 4, wherein a multiplicity of latching elements and counter latching elements are provided.

9. An injection device for automatically squeezing out a dosage of injection liquid from a container thereof, the injection device comprising:
- said container configured to hold the injection liquid;
- a housing defining a longitudinal central axis;
- a first component;
- a second component;
- wherein said first component and said second component move relative to one another when the injection liquid is squeezed out;
- an injection spring configured to store energy and to, when the injection liquid is squeezed out from said container, at least partially release said stored energy to cause the dosage of the injection liquid to be squeezed out from said container;
- a setting device to set an injection rate at which the injection liquid is squeezed out from said container;
- said setting device being configured to influence an energy required for moving said second component in relation to said first component;
- said first component, when squeezing out the injection liquid, is guided in said housing so as to be movable in the direction of said longitudinal central axis and so as to be rotationally fixed;
- said second component, when squeezing out the injection liquid, is mounted in relation to said housing so as to be rotatable and so as to be rotationally fixed in the direction of said longitudinal central axis;
- a setting spring; and,
- said setting device including an operating element configured to be pretensioned by said setting spring in a direction counter to an increase in said injection rate.

10. The injection device of claim 9, wherein:
the injection device defines a proximal direction; and,
said operating element forms said first component and, for squeezing out the injection liquid, is to be displaced in said proximal direction, counter to a force exerted by said setting spring.

11. The injection device of claim 10, wherein said setting spring acts between the operating element and the housing.

12. The injection device of claim 10, wherein:
said setting spring has a first end and a second end; and,
said setting spring acts between the operating element and said housing and is supported on said operating element via said first end and is supported on said housing via said second end.

13. An injection device for automatically squeezing out a dosage of injection liquid from a container thereof, the injection device comprising:
- said container configured to hold the injection liquid;
- a housing defining a longitudinal central axis;
- a first component;
- a second component;
- wherein said first component and said second component move relative to one another when the injection liquid is squeezed out;
- an injection spring configured to store energy and to, when the injection liquid is squeezed out from said container, at least partially release said stored energy to cause the dosage of the injection liquid to be squeezed out from said container;
- a setting device to set an injection rate at which the injection liquid is squeezed out from said container;
- said setting device being configured to influence an energy required for moving said second component in relation to said first component;
- said first component, when squeezing out the injection liquid, is guided in said housing so as to be movable in the direction of said longitudinal central axis and so as to be rotationally fixed;
- said second component, when squeezing out the injection liquid, is mounted in relation to said housing so as to be rotatable and so as to be rotationally fixed in the direction of said longitudinal central axis;
- an injection sleeve which, when setting the dosage of the injection liquid, moves in relation to the housing in the direction of said longitudinal central axis;
- said injection spring having a first end and a second end;
- said injection spring being configured as a compression coil spring; and,
- said injection spring being supported in relation to said injection sleeve via said first end and being supported in relation to said housing via said second end.

* * * * *